(12) United States Patent
Doten

(10) Patent No.: US 6,595,071 B1
(45) Date of Patent: Jul. 22, 2003

(54) ESTIMATION OF ERROR ANGLE IN ULTRASOUND FLOW MEASUREMENT

(75) Inventor: Gregory P. Doten, Crystal, MN (US)

(73) Assignee: Transoma Medical, Inc., Arden Hills, MN (US)

(*) Notice: Subject to any disclaimer, the term of this patent is extended or adjusted under 35 U.S.C. 154(b) by 0 days.

(21) Appl. No.: 09/478,762

(22) Filed: Jan. 6, 2000

(51) Int. Cl.$^7$ ................................................. G01L 3/02
(52) U.S. Cl. ................................................. 73/861.29
(58) Field of Search ......................... 73/861.29, 861.28, 73/861.27; 340/870.02, 870.03

(56) References Cited

U.S. PATENT DOCUMENTS

| | | | | |
|---|---|---|---|---|
| 3,575,050 A | * | 4/1971 | Lynnworth | 73/861.28 |
| 4,001,603 A | | 1/1977 | Wilcox | |
| 4,001,680 A | | 1/1977 | Bylund et al. | 324/78 |
| 4,011,503 A | | 3/1977 | Ferrara | 324/83 |
| 4,015,470 A | | 4/1977 | Morrison | 73/194 A |
| 4,022,058 A | | 5/1977 | Brown | 73/194 |
| 4,055,814 A | | 10/1977 | Abraham et al. | |
| 4,068,184 A | | 1/1978 | Ahmed | 330/257 |
| 4,109,523 A | | 8/1978 | Teyssandier | 73/194 A |
| 4,185,498 A | | 1/1980 | Watson et al. | |
| 4,194,166 A | | 3/1980 | Sakai et al. | 330/257 |
| 4,227,407 A | | 10/1980 | Drost | 73/194 |
| 4,265,126 A | | 5/1981 | Papadofrangakis et al. | 73/861 |
| 4,308,754 A | | 1/1982 | Pedersen et al. | 73/861.28 |
| 4,312,238 A | | 1/1982 | Rey | 73/861.28 |
| 4,316,150 A | | 2/1982 | Crosby | 331/1 A |
| 4,365,204 A | | 12/1982 | Haque | 328/127 |
| 4,383,202 A | | 5/1983 | Beck et al. | 315/200 A |
| 4,384,491 A | | 5/1983 | Brown et al. | 73/861.28 |
| 4,452,090 A | | 6/1984 | Kou et al. | 73/861.28 |
| 4,520,319 A | | 5/1985 | Baker | 328/133 |

(List continued on next page.)

FOREIGN PATENT DOCUMENTS

| | | | |
|---|---|---|---|
| CA | 1153795 | 9/1983 | H03L/7/08 |
| DE | 19617635 | 11/1997 | H03L/7/08 |
| EP | 0012058 | 6/1980 | G01F/1/66 |
| EP | 0252444 | 7/1987 | H03L/7/00 |
| EP | 0402711 | 12/1990 | H03L/7/089 |
| EP | 0588599 | 3/1994 | G01F/1/66 |
| EP | 0711041 | 11/1994 | H03L/7/14 |
| EP | 0803984 | 3/1997 | H03L/7/093 |
| WO | WO-98/00685 | 1/1998 | |

OTHER PUBLICATIONS

Drost, C.J., "Vessel Diameter–Independent Volume Flow Measurements Using Ultrasound", *Proceedings of the San Diego Biomedical Symposium*, vol. 17, J. Martin, et al., (Eds.), pp. 299–302, (1978).

Hartley, C.J., "A Phase Detecting Ultrasonic Flowmeter", *25thACEMB*, Americana Hotel, Bal Harbour, FL, Supported by NIH Grant HE–03251–08., 7 p., (Oct. 1972).

Johansson, H.O., "A Simple Precharged CMOS Phase Frequency Detector", *IEEE Journal of Solid–State Circuits*, 33(2), pp. 295–299, (Feb. 1998).

Maeda, T., et al., "An Ultra–Low–Power–Consupmtion High–Speed GaAs Quasi–Differential Switch Flip–Flop (QD–FF)", *IEEE Journal of Solid–State Circuits*, 31(9), pp. 1361–1363, (Sep. 1996).

(List continued on next page.)

*Primary Examiner*—Harshad Patel
(74) *Attorney, Agent, or Firm*—Schwegman, Lundberg, Woessner & Kluth, P.A.

(57) ABSTRACT

A method for estimating fluid flow in a conduit using a probe with four transducers is provided. The method includes generating two transit time measurements and compensating for an error angle in the transit time measurements using a predetermined compensation factor. The method further includes generating a flow measurement and estimating fluid flow based on the flow measurement.

33 Claims, 14 Drawing Sheets

U.S. PATENT DOCUMENTS

| | | | |
|---|---|---|---|
| 4,524,333 A | 6/1985 | Iwata et al. | 331/17 |
| 4,557,148 A | 12/1985 | Akiyama | 73/861.28 |
| 4,585,989 A | 4/1986 | Matney | 324/83 |
| 4,629,914 A | 12/1986 | Okanobu | 307/510 |
| 4,633,719 A | 1/1987 | Vander Heyden | 73/861.28 |
| 4,808,856 A | 2/1989 | Tanigawa | 307/511 |
| 4,870,303 A | 9/1989 | McGinn | 328/155 |
| 4,922,750 A * | 5/1990 | Magori | 73/861.29 |
| 4,947,852 A | 8/1990 | Nassi et al. | 128/662.06 |
| 5,035,147 A | 7/1991 | Woodward | 73/861.28 |
| 5,078,148 A | 1/1992 | Nassi et al. | 128/661.09 |
| 5,103,123 A | 4/1992 | McGinn | 307/514 |
| 5,117,698 A | 6/1992 | Baumoel | 73/861.28 |
| 5,121,639 A | 6/1992 | McShane | |
| 5,121,749 A | 6/1992 | Nassi et al. | 128/692 |
| 5,142,555 A | 8/1992 | Whiteside | 375/81 |
| 5,200,980 A | 4/1993 | Briddell | 375/83 |
| 5,339,816 A | 8/1994 | Akamatsu et al. | 128/661.09 |
| 5,440,936 A | 8/1995 | Spani et al. | 73/861.28 |
| 5,461,921 A | 10/1995 | Papadakis et al. | |
| 5,502,652 A | 3/1996 | Hoggatt et al. | 364/510 |
| 5,515,721 A | 5/1996 | Kim et al. | 73/170.13 |
| 5,553,505 A | 9/1996 | Bignell et al. | 73/861.28 |
| 5,577,079 A | 11/1996 | Zenno et al. | 375/373 |
| 5,585,756 A | 12/1996 | Wang | 327/341 |
| 5,659,268 A | 8/1997 | Kesner | 331/1 A |
| 5,663,666 A | 9/1997 | Chu et al. | 327/7 |
| 5,669,685 A | 9/1997 | Kotani et al. | 353/28 |
| 5,694,062 A | 12/1997 | Welch et al. | 327/3 |
| 5,695,092 A | 12/1997 | Schrandt | |
| 5,747,689 A | 5/1998 | Hampo et al. | |
| 5,757,868 A | 5/1998 | Kelton et al. | 375/360 |
| 5,767,736 A | 6/1998 | Lakshmikumar et al. | 327/536 |
| 5,774,084 A | 6/1998 | Brombaugh et al. | 341/152 |
| 5,785,657 A | 7/1998 | Breyer et al. | 600/454 |
| 5,865,749 A | 2/1999 | Doten et al. | |
| 5,953,386 A | 9/1999 | Anderson | 375/376 |
| 5,970,106 A | 10/1999 | Izumikawa | 375/376 |
| 6,183,423 B1 | 2/2001 | Gaumond et al. | 600/529 |
| 6,205,687 B1 * | 3/2001 | Rocke | 37/348 |
| 6,346,081 B1 | 2/2002 | Vilkomerson | 600/454 |

OTHER PUBLICATIONS

Nagata, M., "A PWM Signal Processing Core Circuit Based on a Switched Current Integration Technique", *IEEE Journal of Solid–State Circuits, 33* (*1*), pp. 53–60, (Jan. 1998).

Rothermel, A., et al., "Analog Phase Measuring Circuit for Digital CMOS IC's", *IEEE Journal of Solid–State Circuits, 28* (*7*), pp. 853–856, (Jul. 1993).

Somasekhar, D., et al., "Differential Current Switch Logic: A Low Power DCVS Logic Family", *IEEE Journal of Solid–State Circuits, 31*(*7*), pp. 981–991, (Jul. 1996).

Soyuer, M., et al., "High–Frequency Phase–Locked Loops in Monolithic Bipolar Technology", *IEEE Journal of Solid–State Circuits, 24* (*3*), pp. 787–795, (Jun. 1989).

"Extracorporeal—www.transonic.com—Transonic Extracorporeal Products", http://www.transonic.com/body_extracorporeal.html, Transonic Systems Inc., Ithaca, NY, 7 pages, (Jul. 1996; Nov.).

"Manual for SYSTEM 5 SVT2 MODULE, Triton Technology, Inc.", 1–18, (Jun. 16, 1997).

* cited by examiner

ESTIMATION OF ERROR ANGLE IN ULTRASOUND FLOW MEASUREMENT

CROSS REFERENCE TO RELATED CASES.

This application is related to the following commonly assigned, co-pending applications:

application Ser. No. 09/478,486, entitled "PHASE DETECTOR" and filed on Jan. 6, 2000 (the '044 Application); and application Ser. No. 09/479,268, entitled "MULTI-PLEXED PHASE DETECTOR" and filed on Jan. 6, 2000 (the '046 Application);

The '044 and '046 Applications are incorporated herein by reference.

NOTICE OF FEDERALLY SPONSORED RESEARCH

Portions of this invention may have been developed under Contract No. 1 R43 HL62803-01A1, awarded by the National Institutes of Health. Therefore, the U.S. Government may-have a paid-up license in portions of this invention and the right, in limited circumstances, to require the patent owner to license others on reasonable terms as provided for by the terms of the contract.

TECHNICAL FIELD OF THE INVENTION

The present invention relates to measuring fluid flow and in particular to compensating for errors in measuring fluid flow.

BACKGROUND

There are many applications for measuring the volumetric flow of fluid within a conduit. In particular in clinical and research medicine the measurement or estimation of volumetric blood flow within a blood vessel is desirable. One method of measurement comprises using transit time to estimate volumetric fluid flow. Transducers made from piezo-electric ceramic material, referred to as crystals, transmit and receive sound energy. Typically, these transducers operate at ultrasound frequencies from tens of Kilohertz to tens of Megahertz. Various methods of performing transit time measurements are available. One method of performing transit time measurements involves using sound. Transit time measures differences in time sound takes to transit an upstream and downstream path in a flowing medium. This difference in transit time is proportional to the velocity of the flowing medium. When a conduit is fully illuminated, the difference in time is proportional to the volumetric flow.

Some transit time measurement systems include only one pair of crystals positioned on opposite sides of a conduit, these crystals simultaneously transmit signals through the conduit to be received by the opposite crystal. The signals are time-shifted by the fluid and measurements are calculated based on the time shifted signals. These measurements include time measurements, flow velocity and volumetric fluid flow.

One problem with transit time measurements is measurement errors due to positioning of crystal probes with respect to the flow of fluid. The problem is that the transit time measurements are dependent upon the angle of the ultrasound path with respect to the flow vector. An angle error can be produced due to a shift in positioning of the probe. For some applications the probes are accessible and can be inspected to determine if the probe has shifted from its original positioning with respect to the flow of fluid. As a result angle error can be corrected by repositioning the probe to its original location or determining the current angle of the signal path with respect to the fluid flow and updating measurement calculations based on the new angle. In other applications, where the probes are not accessible such as in vivo applications, determining whether the probes have shifted and repositioning the probes is very difficult. As a result measurement errors can go undetected and produce significant flow measurement errors.

A system of transit time measurements, developed by Transonic Systems, Inc., attempts to reduce the error caused by angle errors by placing a pair of crystals on the same side of a conduit and bouncing ultrasound signals off of a reflector located opposite from the crystals to the opposite crystal. When an error in positioning occurs, the ultrasound signal path angle increases for one segment of the path and the ultrasound signal path angle decreases the same amount for the second segment. This technique can reduce the angle dependency but does not eliminate it, in addition error angle detection for some applications is not available.

In order to improve on these measurement errors some systems have employed two pairs of crystals. Many systems position the crystals so that the crystal pairs transmit signals which form a path designated as an X pattern through the conduit. In one system, two independent measurements for each pair of crystals is received. The measurements are averaged in order to try and compensate for angle errors. The resulting measurement errors, due to improper positioning with respect to the flow vector, may still be significant. In an alternate system, the crystals transmit from one crystal to another and then the same transmission is repeated along the second path. The system then transmits in the opposite direction. The difference in transit time between the two paths is proportional to the volumetric flow. This is a folded geometry configuration. When the angle of the probe changes on the vessel it gets compensated in one direction with one path, and the other direction with the other path. This method has a tendency to reduce angle error measurement but also does not eliminate it. In addition, the current systems do not provide a method for detecting or compensating for measurement errors due to positioning of the crystals with respect to the fluid flow.

SUMMARY

The above mentioned problems with flow meters and transit time measurements and other problems are addressed by the present invention and will be understood by reading and studying the following specification. A method and apparatus are described which detect and compensate for angle errors in transit time measurements using at least one ratio of transit time measurements.

In one embodiment, a method for estimating fluid flow in a conduit using a probe with four transducers is provided. The method includes generating two transit time measurements and compensating for an error angle in the transit time measurements using a predetermined compensation factor. The method further includes generating a flow measurement and estimating fluid flow based on the flow measurement.

DETAILED DESCRIPTION

The following detailed description refers to the accompanying drawings which form a part of the specification. The drawings show, and the detailed description describes, by way of illustration specific illustrative embodiments in which the invention may be practiced. These embodiments are described in sufficient detail to enable those skilled in the art to practice the invention. Other embodiments may be used and logical, mechanical and electrical changes may be made without departing from the scope of the present invention. The following detailed description is, therefore, not to be taken in a limiting sense.

Figure 1:
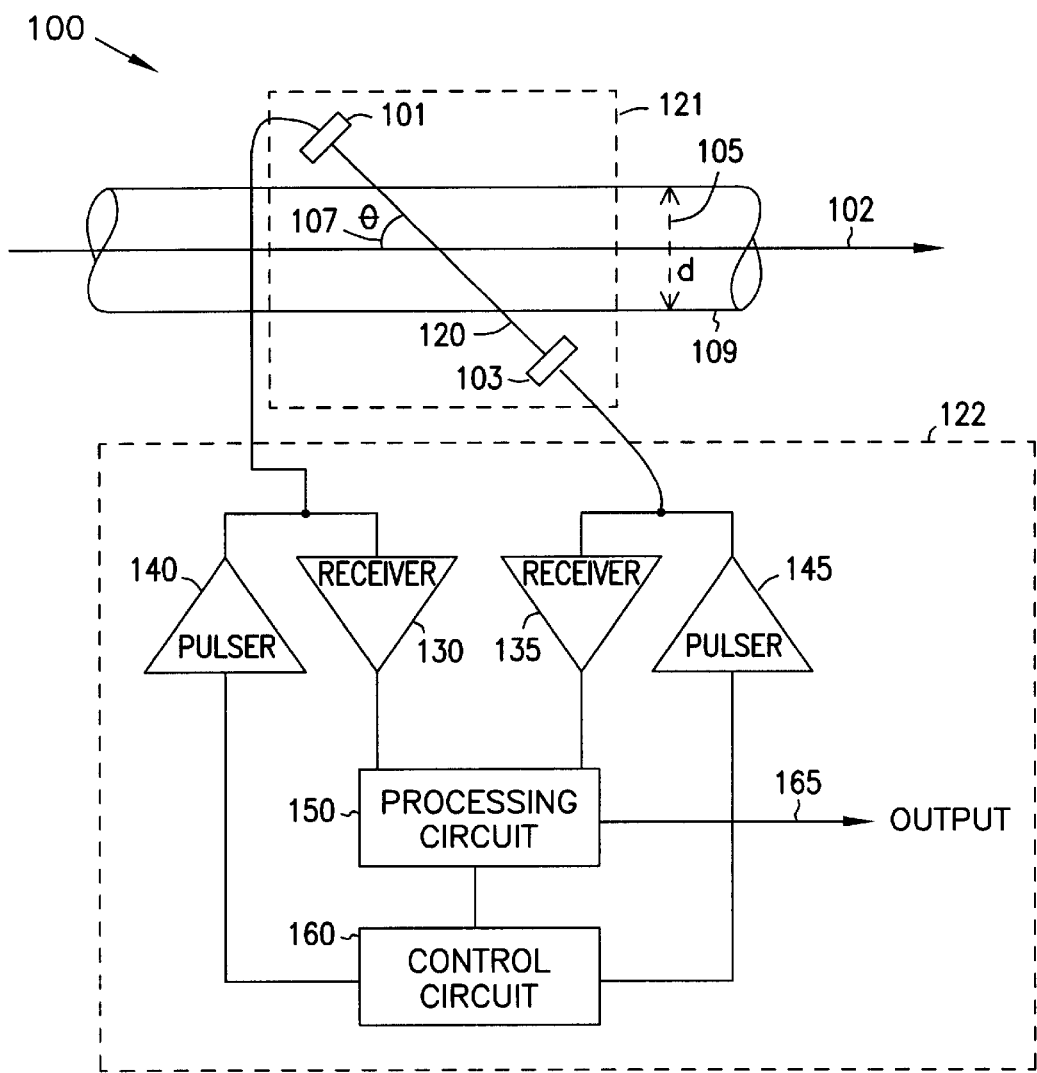
FIG. 1 is a schematic of a two crystal transit time flow meter.

Shown in FIG. 1 is a schematic of a transit time flow meter 100 with a probe 121 around conduit 109 and associated electronics package 122. Currently when measuring flow with a transit time flow meter a flow probe 121, with two crystals 101 and 103 located on opposite sides of a conduit or blood vessel 109, is used. Transducer 101 is connected to its own pulser 140 and receiver 130. Transducer 103 is connected to its own pulser 145 and receiver 135. The pulsers 140 and 145, which are connected to a control circuit 160, are used to generate an excitation signal for crystals 101 and 103 respectively. The crystals 101 and 103 transfer the excitation energy to ultrasound pressure energy which transverses the ultrasound path 120 where it impinges on the opposite crystal. The crystals 101 and 103 convert the ultrasound pressure energy to an electrical voltage. The received signals at crystals 101 and 103 are detected and amplified by receivers 130 and 135 respectively. The outputs of receivers 130 and 135 are connected to the inputs of processing circuit 150 and produces output signals at node 165. Processing circuit 150 includes a phase detector which generates output signals at node 165. The output signals are proportional to the phase difference in the two received ultrasound signals. The intended application is to measure blood flow although other vessels or conduits may be used and blood is not the only fluid which the flow meter can measure. Other fluids may include but are not limited to water, oil, sewage and a variety of chemical solutions.

One problem is that the transit-time measurement is dependent upon the angle 107 that the ultrasound beam 120 forms with the flow vector 102 of the fluid. In many applications and in particular in vivo applications, this angle 107 can change without detection. The result is an unknown error in the flow measurement. Equation 1 illustrates the angle 107 dependency:

$$\Delta\phi = 4\pi\frac{dv}{c\lambda}\cot\theta \qquad (1)$$

where:

$\Delta\phi$ is the difference in phase in radians $v$ is the velocity of the fluid $d$ is the diameter 105 of the conduit 109

$c$ is the speed of sound $\lambda$ is the acoustical wavelength $\theta$ is the angle 107 formed between the ultrasound path 120 and the flow vector 102

Figure 2:
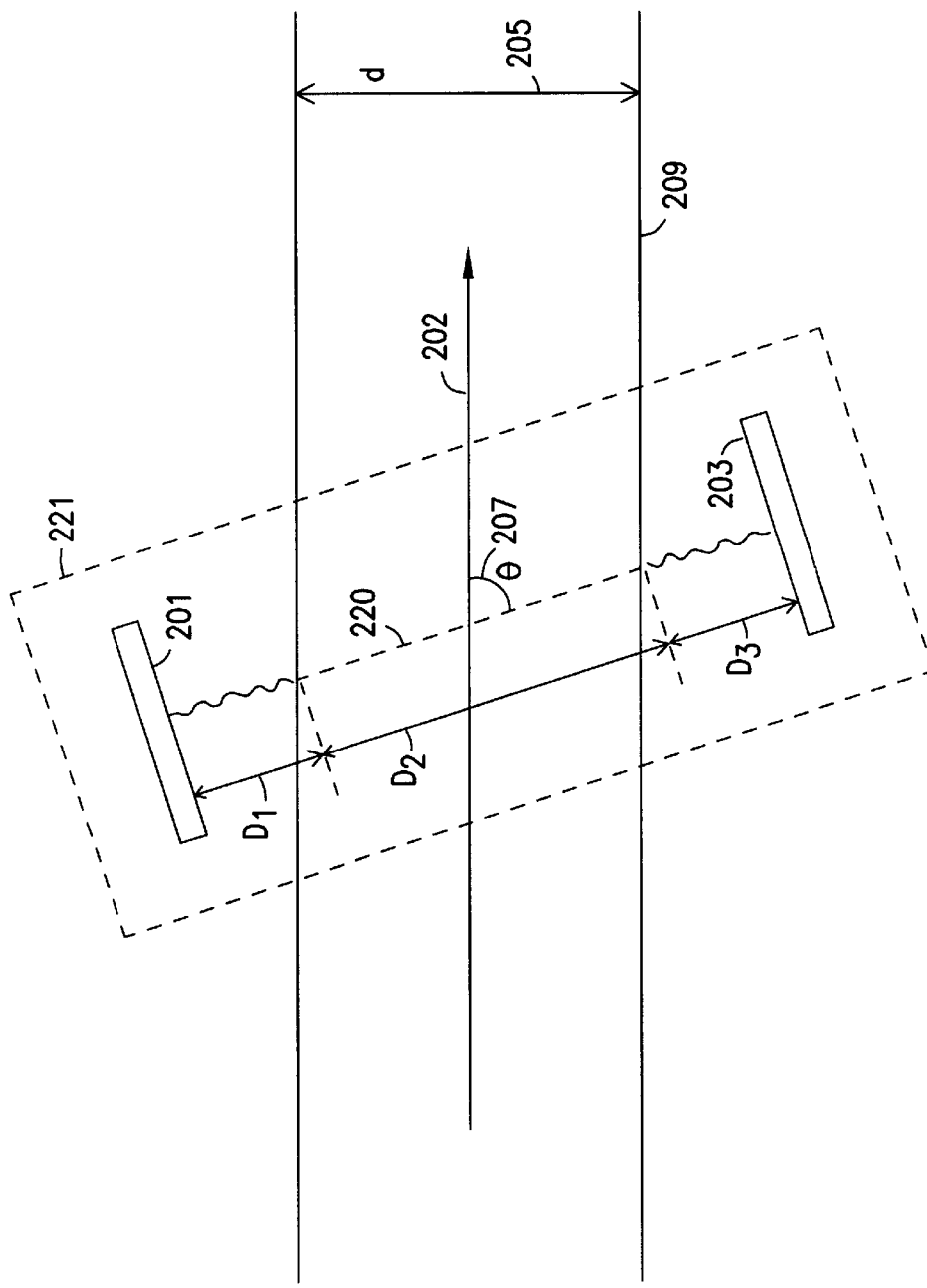
FIG. 2 is a schematic of a cross section of a two crystal transit time flow probe.

One transit time method using a two crystal probe 221 as shown in FIG. 2 involves simultaneously transmitting a burst of ultrasound energy from transducers 201 and 203 creating an ultrasound path 220. With no flow in the conduit 209 the time to transverse the distance $(D_1+D_2+D_3)$ between the two transducers 201 and 203, from 201 to 203 and from 203 to 201, is shown by equations 2 and 3 below, respectively.

$$T_{(201-203)} = \frac{D_1 + D_2 + D_3}{c} \qquad (2)$$

$$T_{(203-201)} = \frac{D_3 + D_2 + D_1}{c} \qquad (3)$$

where:

$c$ is the speed of sound $D_2$ is $d/\sin\theta$ (where $d$ is the diameter 205 of the conduit 209 and $\theta$ is the angle 207 formed between the ultrasound path 220 and the flow vector 202)

If the fluid in the conduit 209 is moving at a velocity v, the time to traverse the distance from one transducer to the other transducer is modified while traveling through $D_2$ by v cos θ. Therefore equations 2 and 3 are modified by substituting for the acoustic velocity c, c+v cos θ for the downstream path, from transducer 201 to 203, and c−v cos θ for the upstream path, from transducer 203 to 201. The resulting equations 4 and 5 are shown below.

$$T_{(201-203)} = \frac{D_1 + D_3}{c} + \frac{D_2}{c + v\cos\theta} \qquad (4)$$

-continued $$T_{(203-201)} = \frac{D_1 + D_3}{c} + \frac{D_2}{c - v\cos\theta} \quad (5)$$

The difference in transit times ($\Delta t$) is shown in equations 6 and 7.

$$\Delta t = T_{(201-203)} - T_{(203-201)} = \quad (6)$$
$$\left(\frac{D_1 + D_3}{c} + \frac{D_2}{c + v\cos\theta}\right) - \left(\frac{D_1 + D_3}{c} + \frac{D_2}{c - v\cos\theta}\right)$$

The constant terms $$\frac{D_1 + D_3}{c}$$

cancel out leaving:

$$\Delta t = \quad (7)$$
$$T_{(201-203)} - T_{(203-201)} = \left(\frac{D_2}{c + v\cos\theta}\right) - \left(\frac{D_2}{c - v\cos\theta}\right) = \frac{2D_2 v\cos\theta}{c^2 - v^2\cos^2\theta}$$

when $c^2 >> v^2 \cos^2\theta$ the equation reduces to Equation 8.

$$\Delta t = \frac{2D_2 v \cos\theta}{c^2} \quad (8)$$

Figure 3:
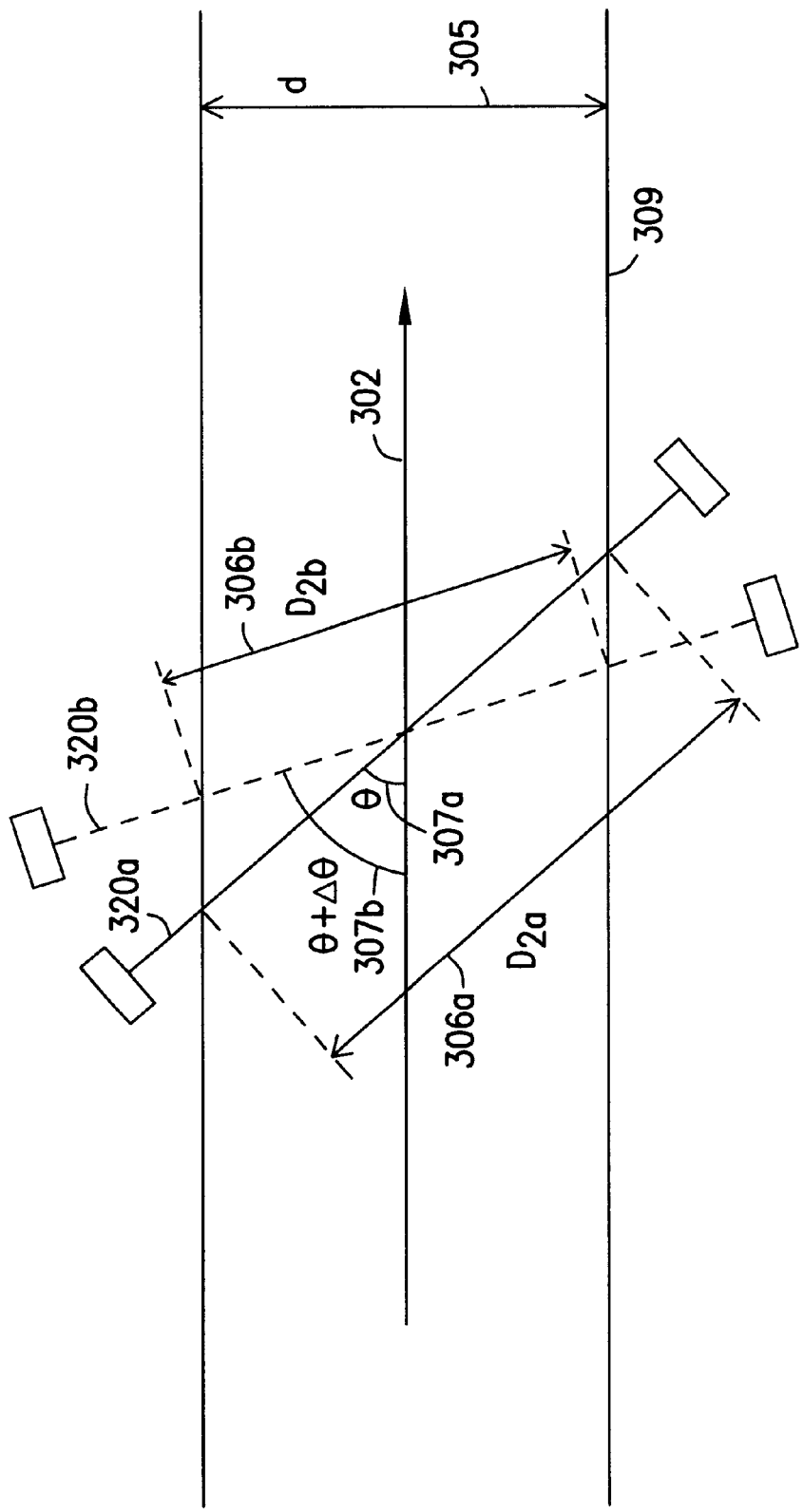
FIG. 3 is a schematic of a cross section of a two crystal transit time flow probe.

For calculating the error analysis, it, is assumed that v and c are constants. FIG. 3 illustrates how the length of the ultrasound path 306, within the conduit 309, changes with respect to angle 307. The only variable is the angle 307 formed between the ultrasound path 320 and the flow vector 302 respectively. Equations 9 and 10 define the lengths of the signal path within the conduit 306a and 306b.

$$D_{2a} = d/\sin\theta \quad (9)$$

$$D_{2b} = d/\sin(\theta + \Delta\theta) \quad (10)$$

where:

d is the diameter 305 of the conduit $\theta$ and $(\theta + \Delta\theta)$ are the angles formed between the ultrasound paths 320a and 320b respectively and the flow vector 302.

$D_{2a}$ is the length of the ultrasound path within the conduit shown as 306a in FIG. 3.

$D_{2b}$ is the length of the ultrasound path within the conduit shown as 306b in FIG. 3.

Substituting d/sin $\theta$ for $D_2$ in equation 8 results in Equation 11 below.

$$\Delta t = \frac{2D_2 v \cos\theta}{c^2} = \frac{2dv\cos\theta}{c^2 \sin\theta} = \frac{2dv}{c^2}\left(\frac{2dv}{c^2} \cdot \frac{\cos\theta}{\sin\theta}\right) = \frac{2dv}{c^2}\cot\theta \quad (11)$$

Equation 12, as shown below is used for error analysis.

$$\% \ error = \frac{true - measured}{true} = \frac{\frac{2dv\cot\theta}{c^2} - \frac{2dv\cot(\theta + \Delta\theta)}{c^2}}{\frac{2dv\cot\theta}{c^2}} \quad (12)$$

For this analysis, the term $$\frac{2dv}{c^2}$$

is a constant and cancels out of the equation, the resulting equation for error analysis in this application is shown in Equation 13 below.

$$\% \ error = \frac{\cot\theta - \cot(\theta + \Delta\theta)}{\cot\theta} \quad (13)$$

Figure 3A:
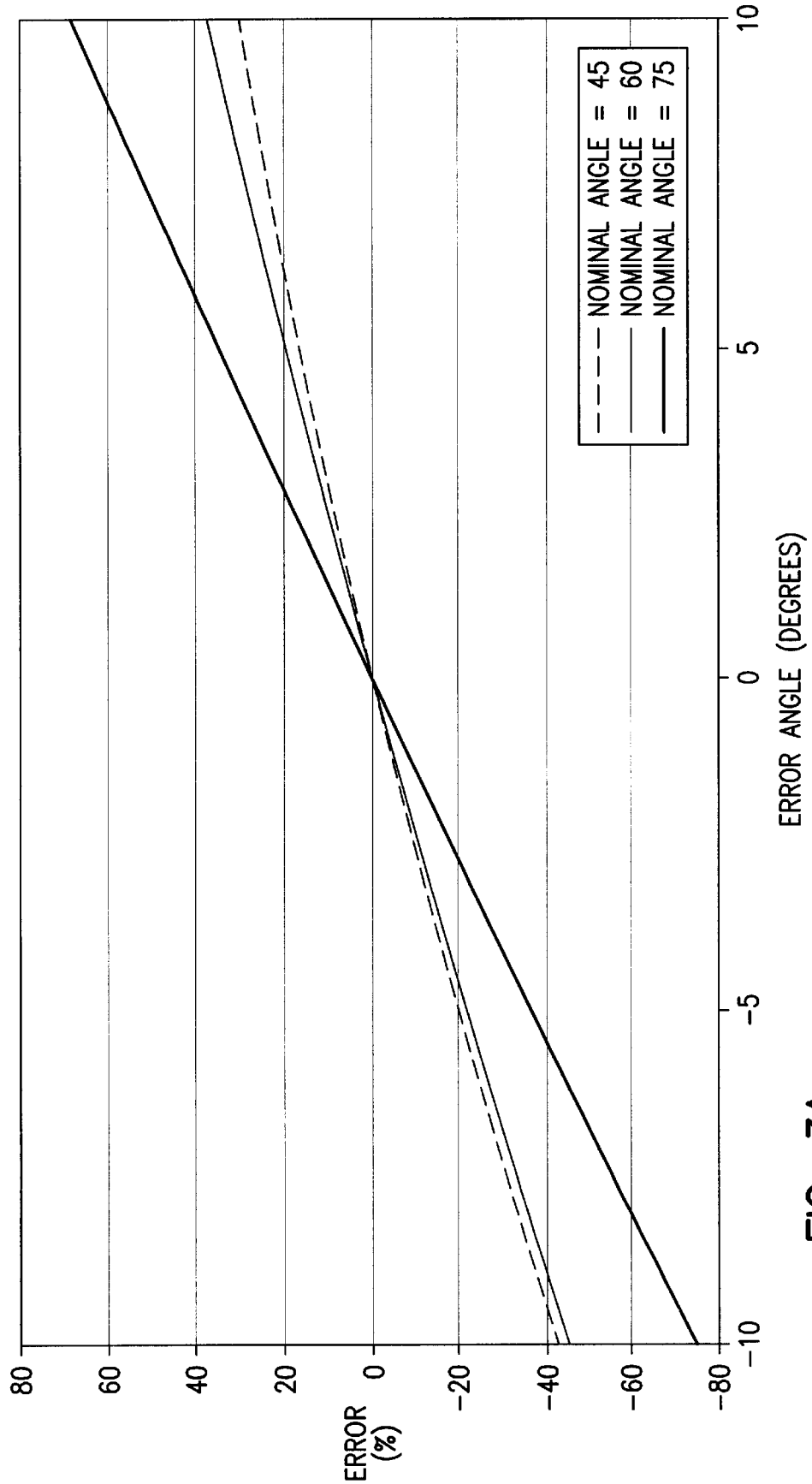
FIG. 3A is a graph illustrating generally percent error versus error angle for a conventional flow meter.

Using a calculation program, the percentage of error for change in angle value in degrees from −10 degrees to +10 degrees for nominal angle values of 45 degrees, 60 degrees and 75 degrees was calculated and is recorded in Table 1. FIG. 3A is a graphical representation of the error analysis. As shown by the calculated values in Table 1 small errors in angle value produces large errors in measured change in time or time shift measurements. These errors are currently undetectable.

TABLE 1

| Error Angle ($\Delta\theta$) | Percentage of Error Nominal Angle = 45 ($\theta_1$) | Percentage of Error Nominal Angle = 60 ($\theta_2$) | Percentage of Error Nominal Angle = 75 ($\theta_3$) |
|---|---|---|---|
| −10 | −42.8 | −45.3 | −74.0 |
| −9 | −37.6 | −40.3 | −66.2 |
| −8 | −32.7 | −35.3 | −58.4 |
| −7 | −28.0 | −30.5 | −50.8 |
| −6 | −23.5 | −25.8 | −43.3 |
| −5 | −19.2 | −21.3 | −35.8 |
| −4 | −15.0 | −16.8 | −28.5 |
| −3 | −11.1 | −12.5 | −21.3 |
| −2 | −7.2 | −8.2 | −14.1 |
| −1 | −3.6 | −4.1 | −7.0 |
| 0 | 0.0 | 0.0 | 0.0 |
| 1 | 3.4 | 4.0 | 6.9 |
| 2 | 6.7 | 7.9 | 13.8 |
| 3 | 10.0 | 11.7 | 20.7 |
| 4 | 13.1 | 15.5 | 27.5 |
| 5 | 16.1 | 19.2 | 34.2 |
| 6 | 19.0 | 22.9 | 40.9 |
| 7 | 21.9 | 26.5 | 47.5 |
| 8 | 24.6 | 30.0 | 54.2 |
| 9 | 27.3 | 33.5 | 60.8 |
| 10 | 30.0 | 37.0 | 67.3 |

Figure 4:
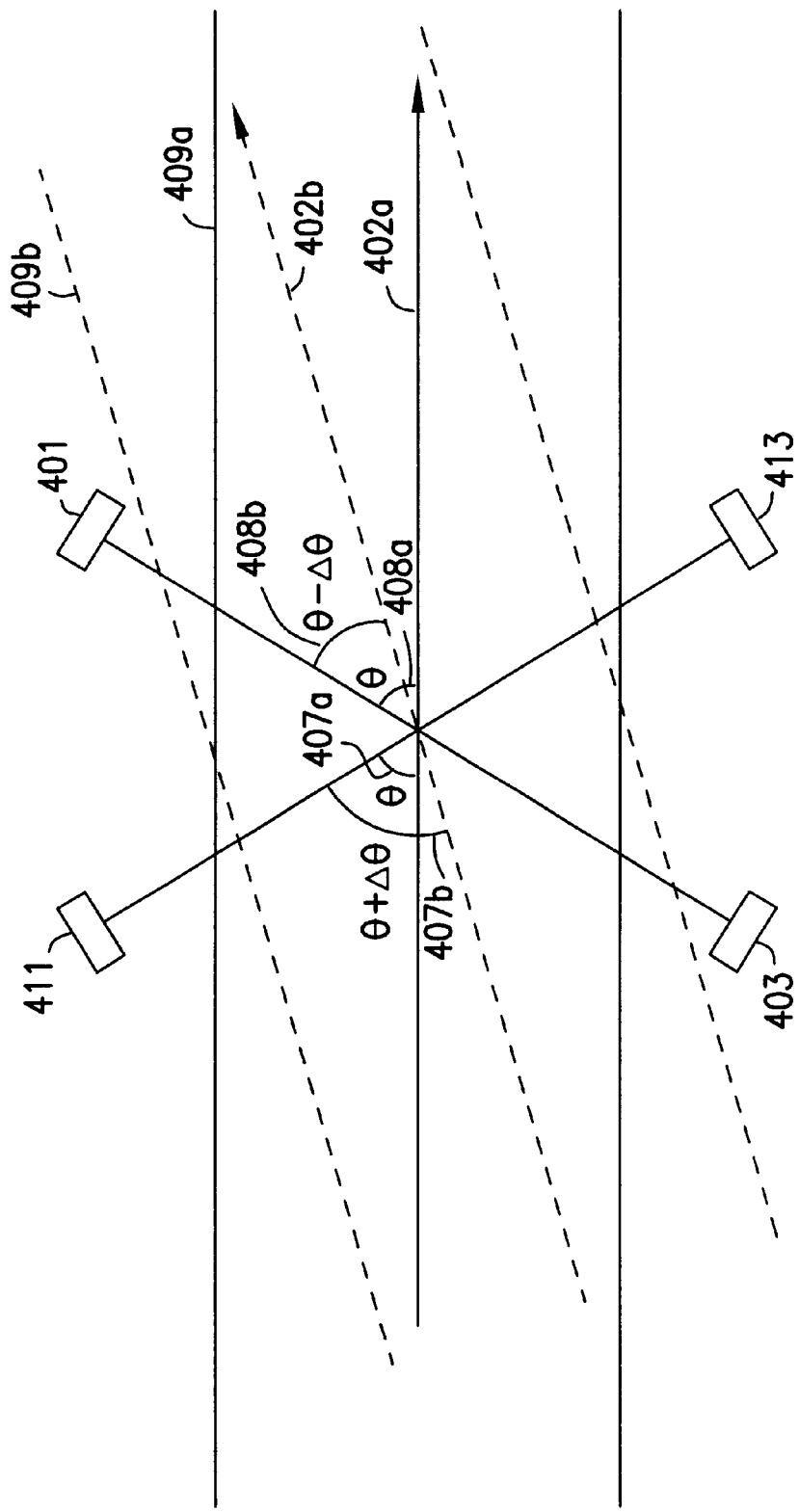
FIG. 4 is a schematic of a conventional four crystal transit time flow probe.

One approach to reduce measurement errors caused by angle errors is to use an "X" pattern where four crystals are aligned to operate as pairs. As shown in FIG. 4, these pairs comprise transducers 401 and 403 as one pair and transducers 411 and 413 as another pair. Each pair provides a transit time measurement. An angle error is produced when the probe is shifted in relationship to the flow vector within a conduit. As shown in FIG. 4, 2 pairs of probes 401–403 and 411–413 are shifted in relationship to the flow vector 402 within conduit 409. The shift is depicted in FIG. 4 with the conduit 409a before shifting and conduit 409b after shifting. For probe pair 411–413 the angle shifts from $\theta$ to $(\theta+\Delta\theta)$ for angles 407a and 407b respectively. For probe pair 401–403 angle 408a shifts from $\theta$ to angle 408b ($\theta-\Delta\theta$).

In this embodiment, angle 407a (θ), with respect to the flow vector 402a, for probe pair 411–413 is equal to angle 408a (θ), with respect to flow vector 402a, for probe pair 401–403. In addition, the change in angles 407a and 408a (Δθ) due to a repositioning of the two probe pairs 411–413 and 401–403 with respect to flow vector 402a is equal but opposite. In alternate embodiments, the angles 407a and 408a may not be equal with respect to flow vector 402a but the Δθ due to repositioning would be equal as the probes are stationary in relationship to each other. The two transit time measurements can be processed in several ways, a common method, in order to reduce angle error, is to average the errors caused by the angle error.

Equations 14 through 18 show the derivation of a percentage of error (average) for a four crystal probe. For probe pair 411–413 the change in time measurement is shown in equation 14.

$$\Delta t_{(411\text{-}413)} = \frac{2dv}{c^2}\cot(\theta + \Delta\theta) \quad (14)$$

where:

θ is the angle 407a formed between the ultrasound path 420 and the flow vector 402a.

θ + Δθ is the angle 407b formed between the ultrasound path 420 and the flow vector 402b.

For probe pair 401–403, the change in time measurement is shown in equation 15.

$$\Delta t_{(401\text{-}403)} = \frac{2dv}{c^2}\cot(\theta - \Delta\theta) \quad (15)$$

where:

θ is the angle 408a formed between the ultrasound path 422 and the flow vector 402a.

θ − Δθ is the angle 408b formed between the ultrasound path 422 and the flow vector 402b.

Using similar analysis as with the two crystal probe for the percentage of error calculation the percentage of error calculation is shown as equations 16 and 17.

For probe pair 411-413:

$$\% \, error_{(411\text{-}413)} = \frac{\cot(\theta) - \cot(\theta + \Delta\theta)}{\cot(\theta)} \quad (16)$$

For probe pair 401-403:

$$\% \, error_{(401\text{-}403)} = \frac{\cot(\theta) - \cot(\theta - \Delta\theta)}{\cot(\theta)} \quad (17)$$

Averaging the percent error for improved error angles results in equation 18.

$$\% \, error \, (average) = \frac{\% \, error_{(411\text{-}413)} + \% \, error_{(401\text{-}403)}}{2} \quad (18)$$

Figure 4A:
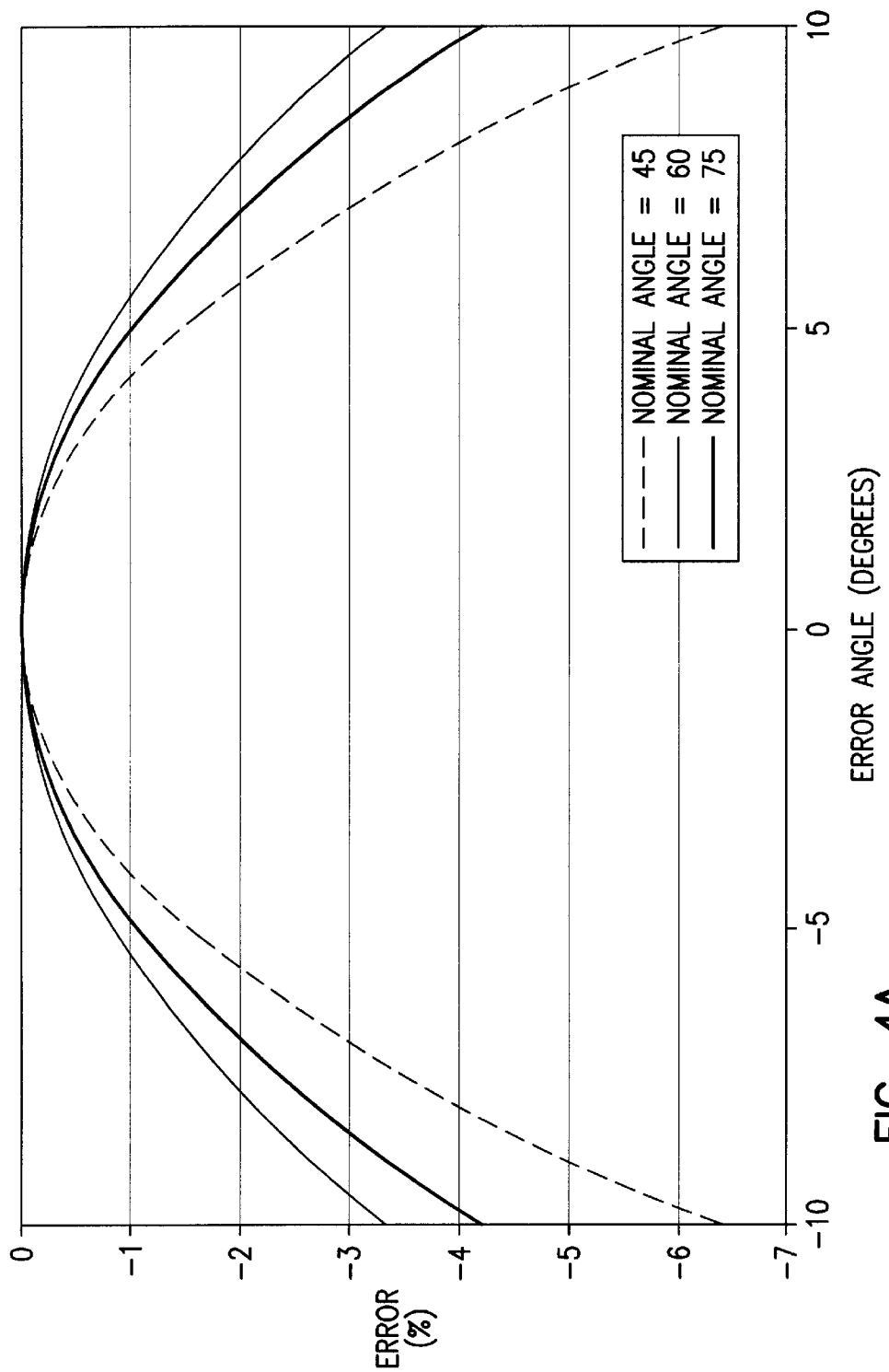
FIG. 4A is a graph illustrating generally percent error versus error angle for a conventional flow meter.

Using a calculation program the percent error average for a four probe crystal can be calculated. A set of calculations was performed for changes in angle value in degrees from −10 deg to +10 degrees for nominal angle values of 45 degrees, 60 degrees and 75 degrees and is recorded in Table 2. FIG. 4A is a graphical representation of the error analysis.

As shown by the calculated values in Table 2 the errors are reduced by the simple method of averaging. Although the errors still are not detectable.

TABLE 2

| Error Angle (Δθ) | Percentage of Error Nominal Angle = 45 ($\theta_1$) | Percentage of Error Nominal Angle = 60 ($\theta_2$) | Percentage of Error Nominal Angle = 75 ($\theta_3$) |
|---|---|---|---|
| −10 | −6.42 | −4.19 | −3.34 |
| −9 | −5.15 | −3.37 | −2.69 |
| −8 | −4.03 | −2.65 | −2.12 |
| −7 | −3.06 | −2.02 | −1.62 |
| −6 | −2.23 | −1.48 | −1.18 |
| −5 | −1.54 | −1.02 | −0.82 |
| −4 | −0.98 | −0.65 | −0.52 |
| −3 | −0.55 | −0.37 | −0.29 |
| −2 | −0.24 | −0.16 | −0.13 |
| −1 | −0.06 | −0.04 | −0.03 |
| 0 | 0.00 | 0.00 | 0.00 |
| 1 | −0.06 | −0.04 | −0.03 |
| 2 | −0.24 | −0.16 | −0.13 |
| 3 | −0.55 | −0.37 | −0.29 |
| 4 | −0.98 | −0.65 | −0.52 |
| 5 | −1.54 | −1.02 | −0.82 |
| 6 | −2.23 | −1.48 | −1.18 |
| 7 | −3.06 | −2.02 | −1.62 |
| 8 | −4.03 | −2.65 | −2.12 |
| 9 | −5.15 | −3.37 | −2.69 |
| 10 | −6.42 | −4.19 | −3.34 |

Figure 4B:
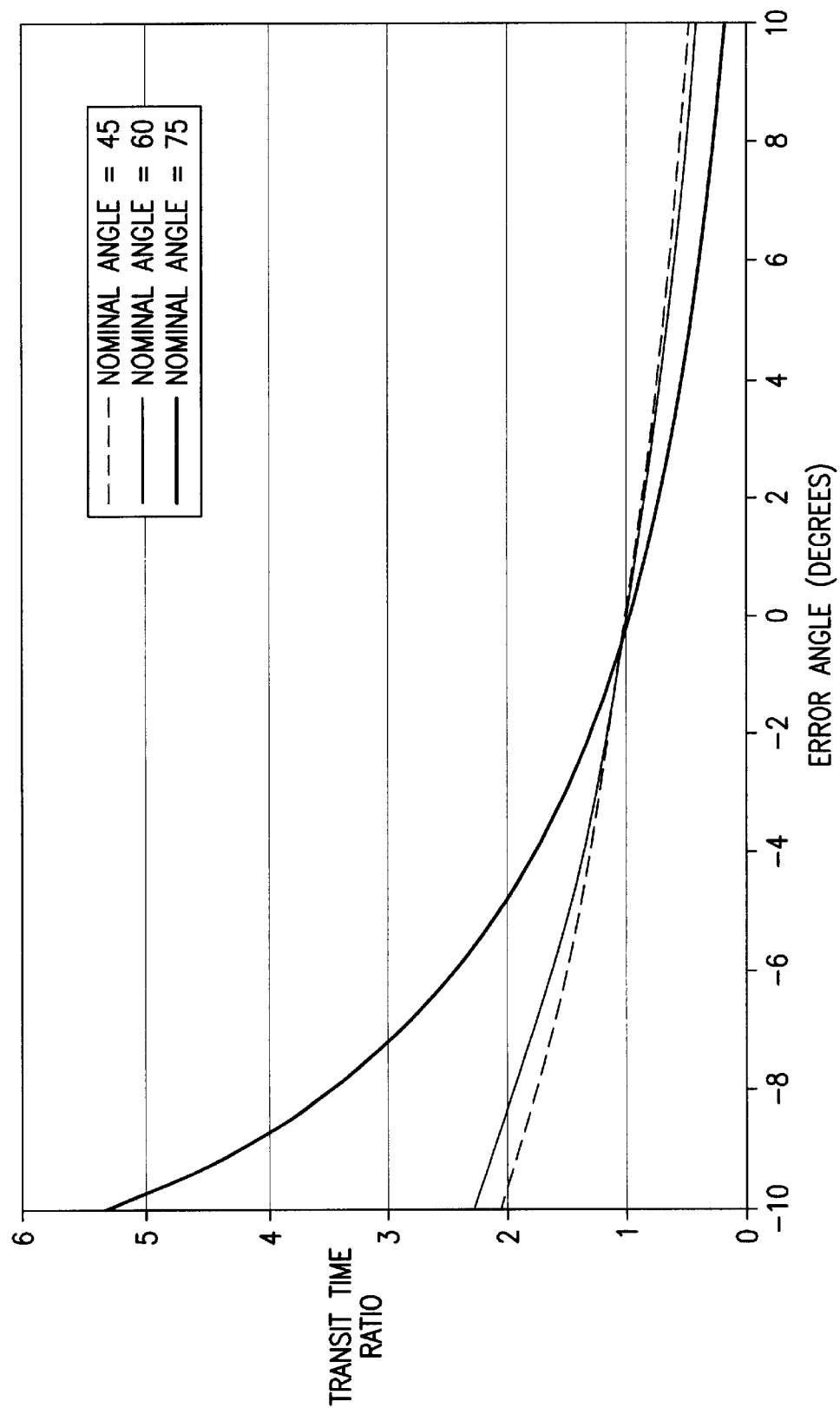
FIG. 4B is a graph illustrating generally transit time ratio versus error angle according to the teachings of the present invention.

Embodiments of the present invention provide an apparatus and a method for estimating an error angle in a four crystal system to compensate for errors introduced by improper placement of the crystals or movement of the crystals with respect to the flow vector of a fluid within a conduit. This is accomplished by calculating a ratio based on transit time measurements and then determining a correction factor or error compensation value. In one embodiment, determining a correction factor or error compensation is accomplished by calculating a correction factor using a mathematical function, e.g. a polynomial fit, based on the curves for the ratio to estimate angle errors as shown in FIG. 4B. In another embodiment, determining a correction factor is accomplished by retrieving error angle values from a look-up table as shown below in Table 3. In equation 19, a transit time ratio is derived for use with calculating look-up tables for correction of error angles.

$$\frac{\Delta t_{(411\text{-}413)}}{\Delta t_{(401\text{-}403)}} = \frac{\frac{2dv}{c^2}\cot(\theta + \Delta\theta)}{\frac{2dv}{c^2}\cot(\theta - \Delta\theta)} = \frac{\Delta t_{(411\text{-}413)}}{\Delta t_{(401\text{-}403)}} = \frac{\cot(\theta + \Delta\theta)}{\cot(\theta - \Delta\theta)} = \frac{\tan(\theta - \Delta\theta)}{\tan(\theta + \Delta\theta)} \quad (19)$$

Using the transit time ratio derived from equation 19, transit time ratios for nominal value angles 45, 60 and 75 degrees were calculated and recorded in a look-up table, Table 3 below. FIG. 4B is a graphical representation of the ratio to estimate angle errors.

TABLE 3

| Error Angle | Transit Time Ratio Nominal Angle = 45 | Transit Time Ratio Nominal Angle = 60 | Transit Time Ratio Nominal Angle = 75 |
|---|---|---|---|
| −10 | 2.04 | 2.31 | 5.33 |
| −9 | 1.89 | 2.10 | 4.24 |

TABLE 3-continued

| Error Angle | Transit Time Ratio Nominal Angle = 45 | Transit Time Ratio Nominal Angle = 60 | Transit Time Ratio Nominal Angle = 75 |
| --- | --- | --- | --- |
| −8 | 1.76 | 1.93 | 3.46 |
| −7 | 1.64 | 1.77 | 2.87 |
| −6 | 1.52 | 1.63 | 2.42 |
| −5 | 1.42 | 1.50 | 2.06 |
| −4 | 1.32 | 1.38 | 1.77 |
| −3 | 1.23 | 1.27 | 1.53 |
| −2 | 1.15 | 1.17 | 1.32 |
| −1 | 1.07 | 1.08 | 1.15 |
| 0 | 1 | 1 | 1 |
| 1 | 0.93 | 0.92 | 0.87 |
| 2 | 0.87 | 0.85 | 0.75 |
| 3 | 0.81 | 0.78 | 0.65 |
| 4 | 0.75 | 0.72 | 0.56 |
| 5 | 0.71 | 0.66 | 0.48 |
| 6 | 0.65 | 0.61 | 0.41 |
| 7 | 0.61 | 0.56 | 0.35 |
| 8 | 0.56 | 0.52 | 0.28 |
| 9 | 0.53 | 0.47 | 0.23 |
| 10 | 0.49 | 0.43 | 0.18 |

Figure 5:
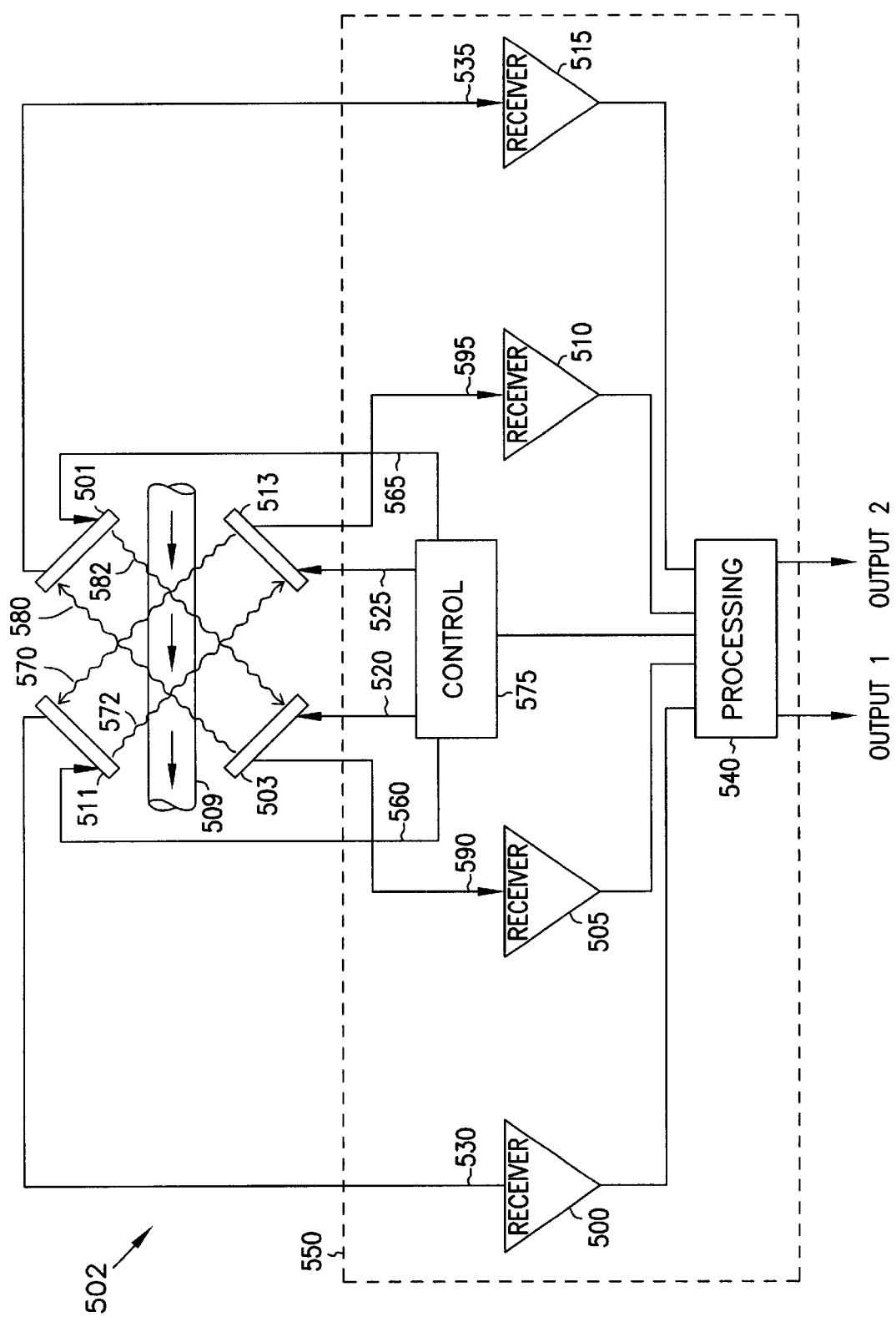
FIG. 5 is a generalized schematic of one embodiment of a flow meter according to the teachings of the present invention.

FIG. 5 is a generalized schematic illustration of one embodiment of an ultrasound flow meter, indicated generally at 502 and constructed according to the teachings of the present invention. A first pair of transducers 501 and 503 and are configured for ultrasonic communication through the conduit 509 which contains a fluid. A second pair of transducers 511 and 513 are similarly configured for ultrasonic communication through the conduit 509. The first pair of transducers 501–503 and the second pair of transducers 511–513 are placed so as to create an "X" pattern with the ultrasound paths 570, 572 and 580, 582 they transmit.

A first burst of ultrasound energy is simultaneously launched from transducers 501 and 503, similarly a second burst of ultrasound energy is simultaneously launched from transducers 511 and 513. In one embodiment the first and second bursts of ultrasound energy are also simultaneous. In an alternate embodiment the first and second bursts of ultrasound energy are sequential. The launched signals are received by the opposite transducer within each pair. For example, transducer 501 launches an ultrasound signal along path shown as 582 which is received, after passing through conduit 509, by transducer 503. Transducer 503 launches an ultrasound signal, along path shown as 580, which is received, after passing through conduit 509, by transducer 501. Similarly transducer 511 launches an ultrasound signal, along path shown as 572, which is received by transducer 513 and transducer 513 launches an ultrasound signal, along path shown as 570, which is received by transducer 511. The signals received by the transducers are time-shifted when transmitted through the conduit 509. The time-shift is a result of fluid flow in conduit 509. Fluid flow is calculated from the difference in transit times of the first pair of ultrasonic signals 570 and 572 and averaged with the difference in transit times of the second pair of ultrasonic signals 580 and 582. Alternate methods of determining fluid flow utilizing the transit time measurements may also be used.

In one embodiment, a control circuit 575 provides an ultrasonic frequency signal to each of the transducers 501, 503, 511 and 513 using nodes 565, 520, 560 and 525 respectively. Control circuit 575 optionally includes pulsers to amplify the ultrasonic signals before providing the signals to the transducers. The pulsers may be internal to the control circuit 575 or external to the control circuit as part of the flow meter circuitry 550.

Each of the transducers 501, 503, 511 and 513 also receive time-shifted ultrasonic paths 580, 582, 570 and 572 and provide resulting electrical signals to receivers 515, 505, 500 and 510 through nodes 535, 590, 530 and 595, respectively. Receivers 500, 505, 510 and 515 provide buffered electrical signals to processing circuit 540. In one embodiment, processing circuit 540 calculates a first transit time measurement from the difference in transit times of the first pair of ultrasonic signals along paths 570 and 572 and a second transit time measurement from the second pair of ultrasonic signals along paths 580 and 582.

In one embodiment, processing circuit 540, which is internal to the flow meter, includes a memory device which stores look up tables containing error angles and corresponding transit time ratios. The processing circuit 540 calculates a transit time ratio based on the first and the-second transit time signals. The processing circuit 540 uses the transit time ratios to retrieve an error angle value. Based on the error angle value, processing circuit 540 calculates corrected transit time measurements, flow measurements and/or volumetric flow measurements.

In another embodiment, processing circuit 540, which is internal to the flow meter includes a memory device having mathematical functions e.g. polynomial fit functions based on the curves for the ratio to estimate angle errors for a plurality of nominal angles. The processing circuit 540 calculates a transit time ratio based on the first and second transit time signals and then uses the mathematical functions to determine an error angle estimate. Based on the error angle estimate, processing circuit 540 calculates corrected transit time measurements, flow measurements and/or volumetric flow measurements.

Figure 5B:
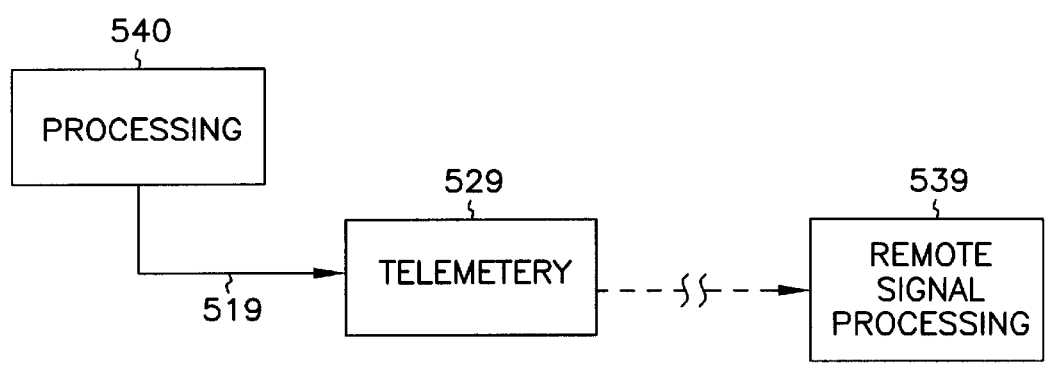
FIG. 5B is a block diagram of an alternate embodiment of a processing circuit with remote processing capabilities according to the teachings of the present invention.

FIG. 5B is a block diagram of an alternate embodiment of a processing circuit with remote processing capabilities. Processing circuit 540 provides through node 519 a first and a second signal containing transit time information to a telemetry device 529 for transmission to a remote signal processing device 539. The remote signal processing device 539 calculates a transit time ratio based on the first and the second transit time signals. The remote signal processing device 539 includes a memory device which stores look up tables with error angles associated with transit time ratios. The tables contain transit time ratios for nominal angles, which can be defined for each application, and error angle estimates based on the ratio. The remote signal processing device 539 then uses the error angle estimates and calculates corrected transit time measurements, using equation 8, flow measurements and/or volumetric flow values.

In another embodiment, processing circuit 540 includes a memory device having mathematical functions e.g. polynomial fit functions which are based on the curves of the ratio to estimate angle errors for a plurality of nominal angles. The remote signal processing device 539 calculates a transit time ratio based on the first and second transit time signals and then uses the mathematical functions to determine an error angle estimate. Based on the error angle estimate, remote signal processing device 539 calculates corrected transit time measurements, flow measurements and/or volumetric flow measurements.

The flow probes may be positioned as an X with angles which are equal in value with relationship to the flow vector of a fluid within a conduit, or which are unequal in value. Further in alternate embodiments, two pairs of flow probes may be positioned in a variety of ways such as opposing each other (\/) and (/\).

Figure 6:
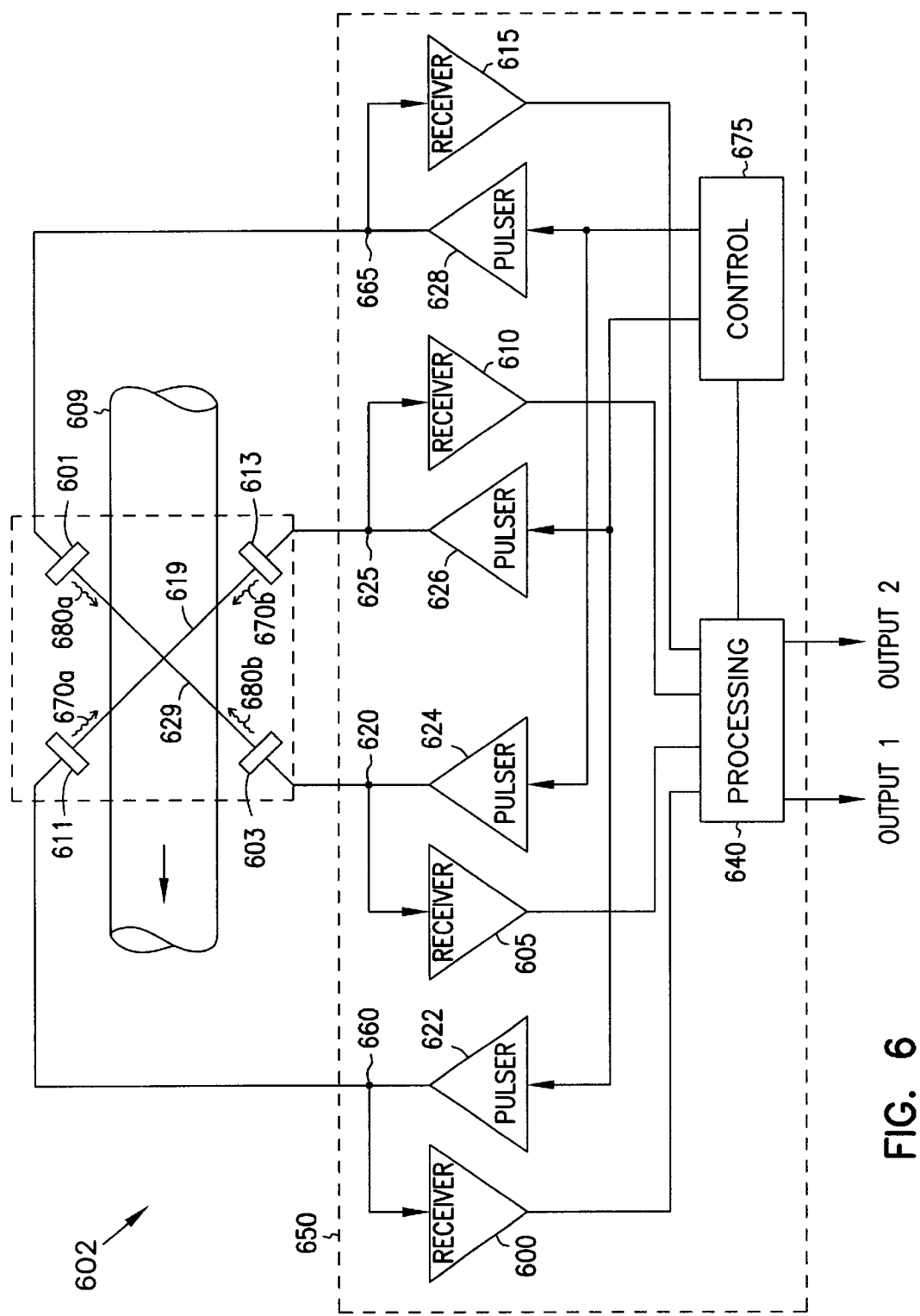
FIG. 6 is a generalized schematic of one embodiment of a flow meter according to the teachings of the present invention.

FIG. 6 is a generalized schematic illustration of one embodiment of an ultrasound flow meter, indicated generally at 605 and constructed according to the teachings of the present invention. A first pair of transducers 601 and 603 and are configured for ultrasonic communication through the conduit 609 which contains a fluid. A second pair of transducers 611 and 613 are similarly configured for ultrasonic communication through the conduit 609. The first pair of transducers 601–603 and the second pair of transducers 611–613 are placed so as to create an "X" pattern with the ultrasound paths 619 and 629 along which they transmit.

A first burst of ultrasound energy, 680*a* and 680*b*, is simultaneously launched from transducers 601 and 603, similarly a second burst of ultrasound energy, 670*a* and 670*b*, is simultaneously launched from transducers 611 and 613. In one embodiment the first and second bursts of ultrasound energy are also transmitted simultaneously. In an alternate embodiment the first and second bursts of ultrasound energy are sequentially transmitted. The launched signals are received by the opposite transducer within each pair. For example, transducer 601 launches an ultrasound signal 680*a* along path shown as 629 which is received, after passing through conduit 609, by transducer 603. Transducer 613 launches an ultrasound signal 670*b*, along path shown as 619, which is received, after passing through conduit 609, by transducer 611. Similarly transducers 603 and 611 launch and 601 and 613 receive respectively. The signals received by the transducers are time-shifted when transmitted through the conduit 609. The time-shift is a result of fluid flow in conduit 609. Fluid flow is calculated from the difference in transit times of the first pair of ultrasonic signals 670*a* and 670*b* and averaged with the difference in transit times of the second pair of ultrasonic signals 680*a* and 680*b*. Alternate methods of determining fluid flow utilizing the transit time measurements may also be used.

In one embodiment, a control circuit 675 provides an ultrasonic frequency signal to each pulser 622, 624, 626 and 628. The pulsers amplify the ultrasonic signals and transmit the amplified signals to the transducers. Each of the transducers 611, 613, 601 and 603 also receive time-shifted ultrasonic signals 670*b*, 670*a*, 680*b* and 680*a* and provide resulting electrical signals to receivers 600, 610, 615 and 605 through nodes 660, 625, 665 and 620, respectively. Receivers 600, 605, 610 and 615 provide buffered electrical signals to processing circuit 640. In one embodiment, processing circuit 640 calculates a first transit time measurement from the difference in transit times of the first pair of ultrasonic signals 670*a* and 670*b* and a second transit time measurement from the second pair of ultrasonic signals 680*a* and 680*b*.

In one embodiment, processing circuit 640, which is internal to the flow meter, includes a memory device which stores look up tables containing error angles and corresponding transit time ratios. The processing circuit 640 calculates a transit time ratio based on the first and the second transit time signals. The processing circuit 640 uses the transit time ratios to retrieve an error angle value. Based on the error angle value, processing circuit 640 calculates corrected transit time measurements, flow measurements and/or volumetric flow measurements.

In another embodiment, processing circuit 640, which is internal to the flow meter, includes a memory device having mathematical functions e.g. polynomial fit functions based on the curves for the ratio to estimate angle errors for a plurality of nominal angles. The processing circuit 640 calculates a transit time ratio based on the first and second transit time signals and then uses the mathematical functions to determine an error angle estimate. Based on the error angle estimate, processing circuit 640 then calculates corrected transit time measurements, flow measurements and/or volumetric flow measurements.

In an alternate embodiment, processing circuit 640 provides a first and a second signal containing transit time information to a telemetry device for transmission to a remote signal processing device. The remote signal processing device calculates a transit time ratio based on the first and the second transit time signals. The remote signal processing device includes a memory device which stores look up tables with error angles associated with transit time ratios. The tables contain transit time ratios for nominal angles, which can be defined for each application, and error angle estimates based on the ratio. The remote signal processing device then uses the error angle estimates and calculates corrected transit time measurements, using equation 8, flow measurements and/or volumetric flow values.

In another embodiment, processing circuit 640 provides a first and a second signal containing transit time-information to a telemetry device for transmission to a remote signal processing device. The remote signal processing device includes a memory device having mathematical functions e.g. polynomial fit functions based on the curves for the ratio to estimate angle errors for a plurality of nominal angles. The remote signal processing device calculates a transit time ratio based on the first and second transit time signals and then uses the mathematical functions to determine an error angle estimate. Based on the error angle estimate, the remote signal processing device calculates corrected transit time measurements, flow measurements and/or volumetric flow measurements.

Figure 7:
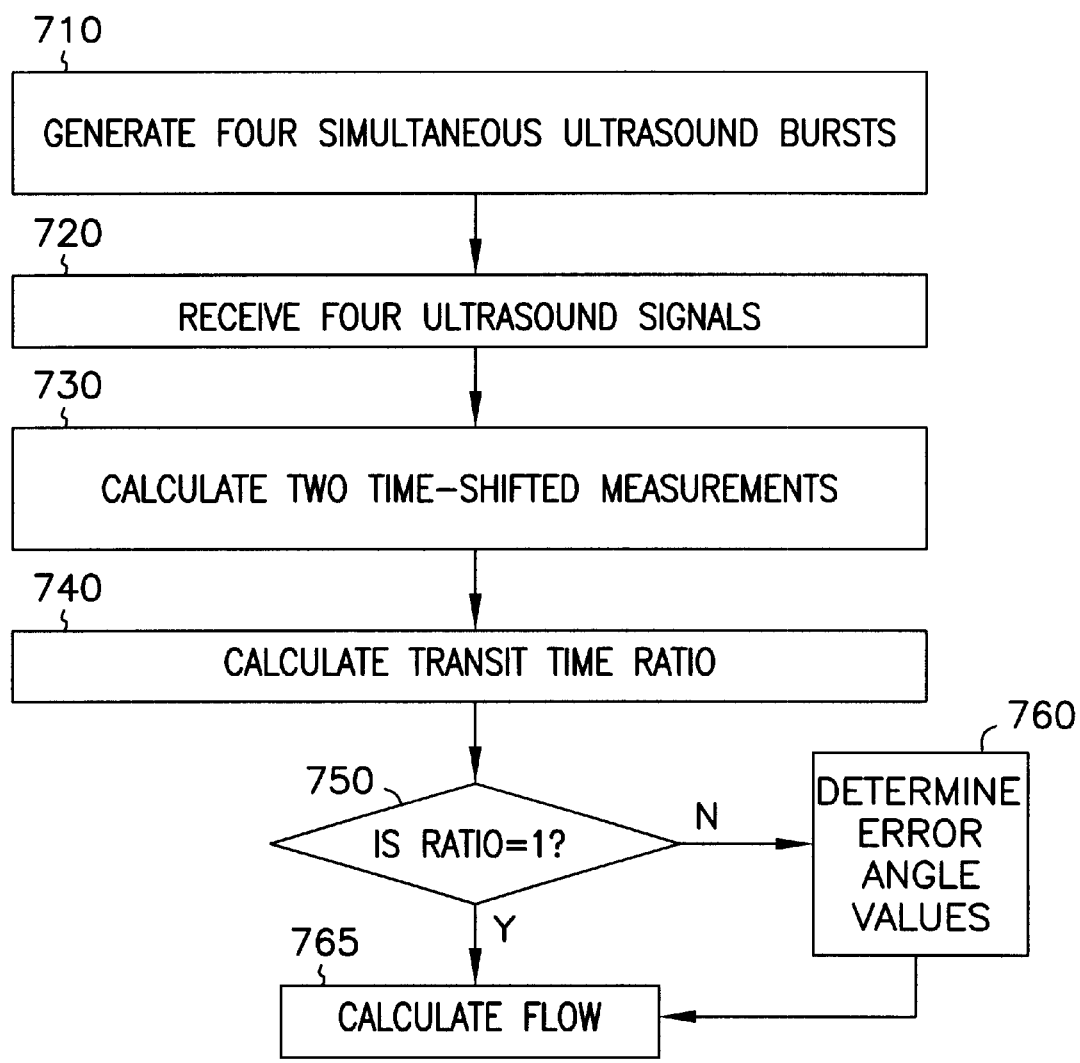
FIG. 7 is a flow chart that illustrates an embodiment of a process of error angle detection and estimation according to the teachings of the present invention.

FIG. 7 is a flow chart of one embodiment of a process of error angle detection and estimation in a flow meter according to the teachings of the present invention. The method begins at block 710 wherein the flow meter generates four simultaneous bursts of ultrasonic energy for transmission through a conduit by two pairs of crystals. The method proceeds to block 720 and the energy signals, which are time shifted, are received by the opposite transducer within each pair. The method proceeds to block 730 and the time-shifted signals are transmitted to a processing circuit which calculates transit time measurements based on the received time-shifted signals. The method proceeds to block 740 and the processing circuit calculates a transit time ratio and proceeds to block 750. When the transit time ratio is equal to 1, there is no angle error detected and the method proceeds to block 765 and calculates flow, e.g., volumetric flow measurements using the transit time measurements calculated at block 730.

When the transit time ratio is not equal to 1, an angle error is detected and the method proceeds to block 760 and determines error angle values based on the transit time ratio. Determining error angle values in one embodiment involves retrieving error angle values from a look-up table. Determining error angle values in alternate embodiments may involve calculating error angle values using mathematical functions e.g. polynomial fit functions based on the curve for the ratio to estimate angle errors. The method then proceeds to block 765 and calculates flow, e.g., volumetric flow values based on the corrected transit time measurements. The method then proceeds to block 710 and repeats the process.

Figure 8:
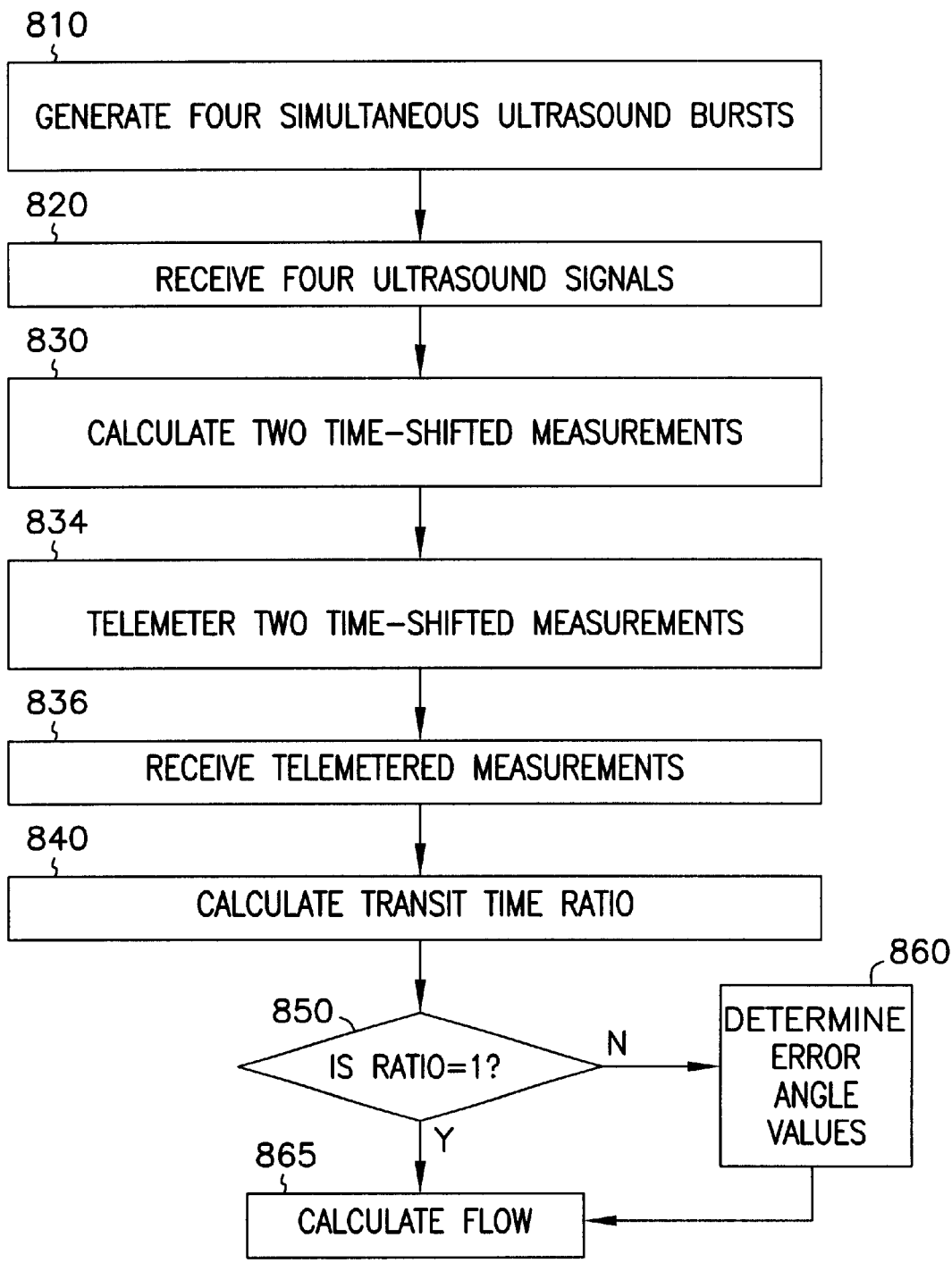
FIG. 8 is a flow chart that illustrates an embodiment of a process of error angle detection and estimation according to the teachings of the present invention.

FIG. 8 is a flow chart of one embodiment of a process of error angle detection and estimation in a flow meter according to the teachings of the present invention. The method begins at block 810 wherein the flow meter generates four simultaneous bursts of ultrasonic energy for transmission through a conduit by two pairs of probes. The method proceeds to block 820 and the energy signals, which are time shifted, are received by the opposite transducer within each pair. The method proceeds to block 830 and the time-shifted signals are transmitted to a processing circuit which calculates transit time measurements based on the received time-shifted signals. The method proceeds to block 834 and telemeters the transit time measurements to an external signal processing circuit. The method then proceeds to block 836 where the external processing circuit receives the telemetered measurements. The method proceeds to block 840 and the processing circuit calculates a transit time ratio and proceeds to block 850. When the transit time ratio is equal to 1, there is no angle error detected and the method proceeds to block 865 and calculates flow, e.g., volumetric flow measurements using the transit time measurements calculated at block 830.

When the transit time ratio is not equal to 1, an angle error is detected and the method proceeds to block 860 and determines error angle values based on the transit time ratio. Determining error angle values in one embodiment involves retrieving error angle values from a look-up table. Determining error angle values in alternate embodiments may involve calculating error angle values using mathematical functions e.g. polynomial fit functions based on the curve for the ratio to estimate angle errors. The method then proceeds to block 865 and calculates flow, e.g., volumetric flow values based on the corrected transit time measurements. The method then proceeds to block 810 and repeats the process.

Figure 9:
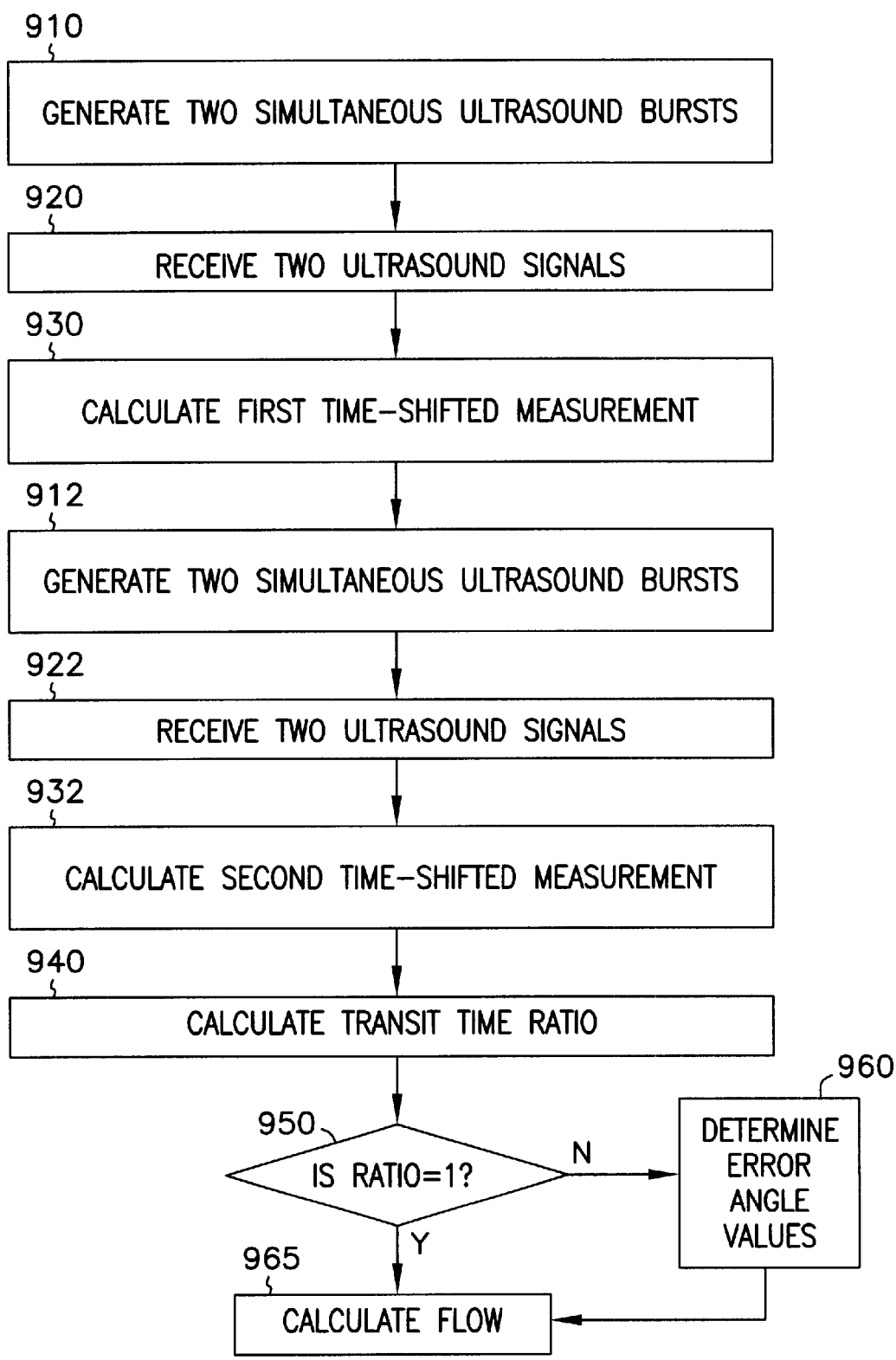
FIG. 9 is a flow chart that illustrates an embodiment of a process of error angle detection and estimation according to the teachings of the present invention.

FIG. 9 is a flow chart of one embodiment of a process of error angle detection and estimation in a flow meter according to the teachings of the present invention. The method begins at block 910 wherein the flow meter generates two simultaneous bursts of ultrasonic energy for transmission through a conduit by one pair of flow probes. The method proceeds to block 920 and the energy signals, which are time shifted, are received by the opposite transducer within the pair. The method proceeds to block 930 and the time-shifted signals are transmitted to a processing circuit which calculates a first transit time measurement based on the received time-shifted signals. The method proceeds to block 912 and the flow meter generates a second set of two simultaneous bursts of ultrasonic energy for transmission through a conduit by a second pair of flow probes. The method proceeds to block 922 and the energy signals, which are time shifted, are received by the opposite transducer within the second pair. The method proceeds to block 932 and the time-shifted signals are transmitted to a processing circuit which calculates a second transit time measurement based on the received time-shifted signals. The method then proceeds to block 940 and the processing circuit calculates a transit time ratio based on the first and second transit time measurements and proceeds to block 950. When the transit time ratio is equal to 1, there is no angle error detected and the method proceeds to block 965 and calculates flow, e.g., volumetric flow measurements using the transit time measurements calculated at blocks 930 and 932.

When the transit time ratio is not equal to 1, angle error is detected and the method proceeds to block 960 and determines error angle values based on the transit time ratio. Determining error angle values in one embodiment involves retrieving error angle values from a look-up table. Determining error angle values in alternate embodiments may involve calculating error angle values using mathematical functions e.g. polynomial fit functions based on the curve for the ratio to estimate angle errors. The method then proceeds to block 965 and calculates flow, e.g., volumetric flow values based on the corrected transit time measurements. The method then proceeds to block 910 and repeats the process.

Figure 10:
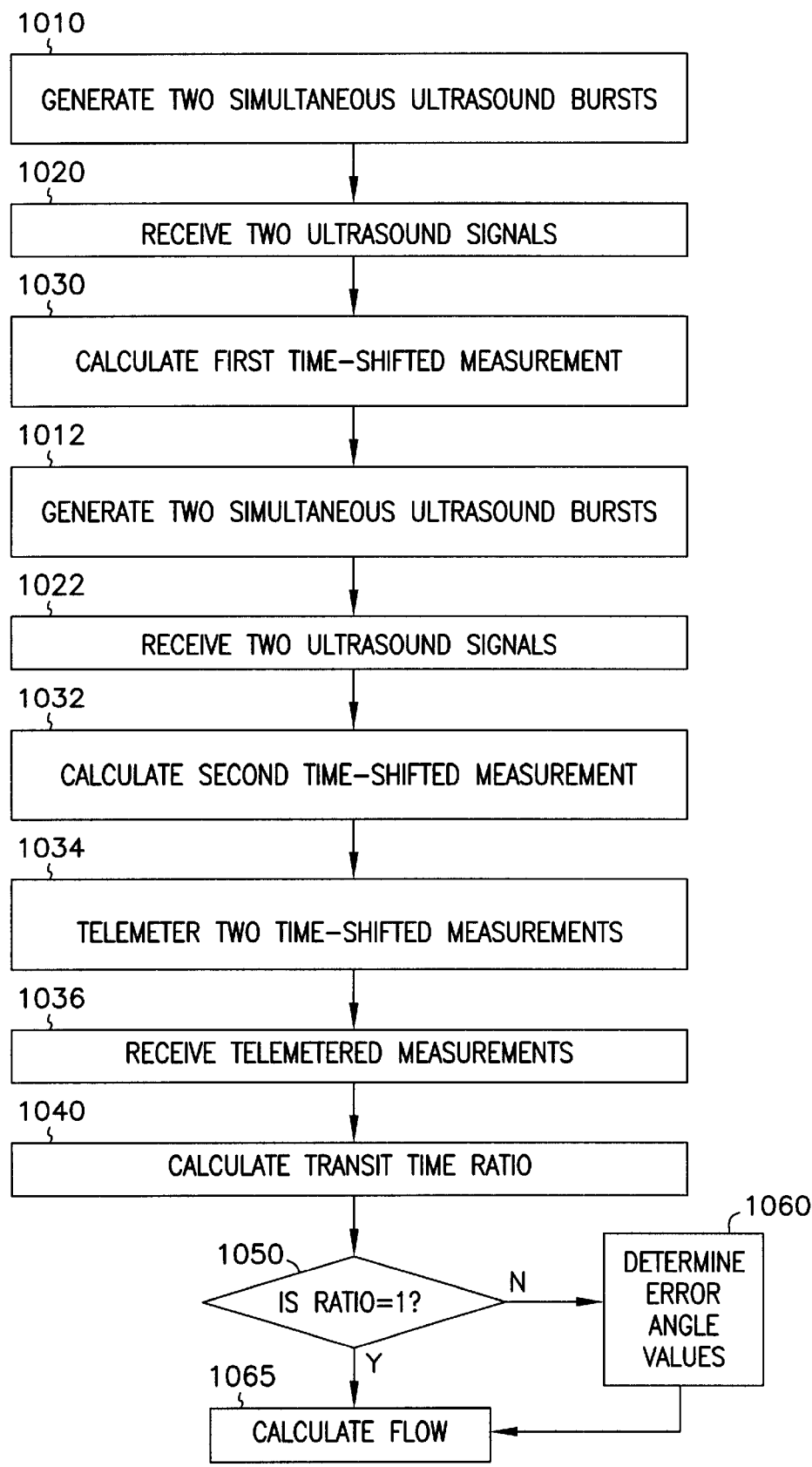
FIG. 10 is a flow chart that illustrates an embodiment of a process of error angle detection and estimation according to the teachings of the present invention.

FIG. 10 is a flow chart of one embodiment of a process of error angle detection and estimation in a flow meter according to the teachings of the present invention. The method begins at block 1010 wherein the flow meter generates two simultaneous bursts of ultrasonic energy for transmission through a conduit by a first pair of flow probes. The method proceeds to block 1020 and the energy signals, which are time shifted, are received by the opposite transducer within the pair. The method proceeds to block 1030 and the time-shifted signals are transmitted to a processing circuit which calculates a first transit time measurement based on the received time-shifted signals. The method then proceeds to block 1012 and the flow meter generates a second set of two simultaneous bursts of ultrasonic energy for transmission through a conduit by a second pair of flow probes. The method proceeds to block 1022 and the energy signals, which are time shifted, are received by the opposite transducer within the second pair. The method proceeds to block 1032 and the time-shifted signals are transmitted to a processing circuit which calculates a second transit time measurement based on the received time-shifted signals. The method proceeds to block 1034 and telemeters the transit time measurements to an external signal processing circuit. The method then proceeds to block 1036 where the external processing circuit receives the telemetered measurements. The method proceeds to block 1040 and the processing circuit calculates a transit time ratio and proceeds to block 1050. When the transit time ratio is equal to 1, there is no angle error detected and the method proceeds to block 1065 and calculates flow, e.g., volumetric flow measurements using the transit time measurements calculated at blocks 1030 and 1032.

When the transit time ratio is not equal to 1, an angle error is detected and the method proceeds to block 1060 and determines error angle values based on the transit time ratio. Determining error angle values in one embodiment involves retrieving error angle values from a look-up table. Determining error angle values in alternate embodiments may involve calculating error angle values using mathematical functions e.g. polynomial fit functions based on the curve for the ratio to estimate angle errors. The method then proceeds to block 1065 and calculates flow, e.g., volumetric flow values based on the corrected transit time measurements. The method then proceeds to block 1010 and repeats the process.

CONCLUSION

Apparatus and methods have been described that detect and compensate for transit time measurement errors in a four crystal probe ultrasonic flow meter. Essentially, an error angle is estimated based on at least one ratio of transit time measurements. This error angle estimate is then used to compensate the transit time measurements for the detected error thereby improving the accuracy of the flow meter.

Although specific embodiments have been illustrated and described herein, it will be appreciated by those of ordinary skill in the art that any arrangement which is, calculated to achieve the same purpose may be substituted for the specific embodiment shown. This application is intended to cover any adaptations or variations of the present invention. For example, this technique can be used with any number measurement systems. Further, the claimed invention is not limited to biomedical applications. Other systems which experience transit time measurement errors can also be improved using error angle detection and correction. Further, bursts of ultrasonic energy provided by crystals or transducers includes as few as a single pulse of ultrasonic energy.

What is claimed is:

1. An apparatus for estimating fluid flow in a conduit, the apparatus comprising:

a probe adapted to be positioned outside a circumference of the conduit, the probe including a first transducer and a second transducer arranged to form a first transmission path through the conduit, and a third transducer and a fourth transducer arranged to form a second transmission path through the conduit, wherein the first transmission path and the second transmission path have a predetermined orientation used to estimate the fluid flow, and wherein an error in positioning the probe introduces an error angle that affects fluid flow estimates;

a control circuit for use to transmit ultrasonic energy along the first transmission path between the first and second transducers, and along the second transmission path between the third and fourth transducers;

a plurality of receivers, wherein each of the plurality of receivers is coupled to one of the at least four transducers to receive a signal representative of received ultrasonic energy that has been time shifted by the fluid flow in the conduit; and a processing circuit, communicatively coupled to the plurality of receivers, to determine a first flow measurement based on the ultrasonic energy received by the first and second transducers along the first transmission path, to determine a second flow measurement based on the ultrasonic energy received by the third and fourth transducers along the second transmission path, to estimate the error angle based on a relationship between the first and second flow measurements, and to compensate for the estimated error angle in fluid flow estimates.

2. The apparatus of claim 1, wherein the processing circuit comprises circuitry which generates a ratio of the first and second flow measurements.

3. The apparatus of claim 2, wherein the processing circuit further includes a memory device which stores angle error look up tables and wherein the processing circuit retrieves angle error values based on the ratio of the two flow measurements and calculates flow velocity and volumetric fluid flow.

4. The apparatus of claim 2, wherein the processing circuit includes a memory device which stores mathematical functions used to determine angle error values based on the ratio of the two flow measurements and wherein the processing circuit calculates angle error values, flow velocity and volumetric fluid flow.

5. The apparatus of claim 1, wherein the processing circuit is integral to the apparatus.

6. The apparatus of claim 1, further comprising:

a telemetry device communicatively coupled to the processing circuit which receives the two flow measurements and telemeters the flow measurements;

a remote signal processing circuit which is wirelessly coupled to the telemetry device and receives the flow measurements and calculates a ratio; and a memory device integral to the processing circuit which includes a memory device which stores angle error look up tables wherein the processing circuit retrieves angle error values based on the ratio of the two flow measurements and calculates flow velocity.

7. The apparatus of claim 1, further comprising:

a telemetry device communicatively coupled to the processing circuit which receives the two flow measurements and telemeters the flow measurements;

a remote signal processing circuit which is wirelessly coupled to the telemetry device and receives the flow measurements and calculates a ratio; and a memory device integral to the processing circuit which includes a memory device which stores mathematical functions for calculating angle error values based on the ratio of the two flow measurements and calculates flow velocity.

8. The apparatus of claim 1, wherein the processing circuit includes a memory device that stores tables of compensation values.

9. The apparatus of claim 1, further comprising an implantable housing containing the control circuit and the processing circuit.

10. The apparatus of claim 1, wherein the fluid is blood and the conduit is a blood vessel.

11. The apparatus of claim 1, wherein the at least four transducers comprise a probe having four crystal transducers.

12. The apparatus of claim 1, wherein the control circuit comprises a plurality of pulsers, wherein each of the plurality of receivers is coupled to the input of at a least one of the four transducers and each pulser amplifies the ultrasonic energy and transmits the amplified energy signals to the at least one transducer.

13. A method of estimating fluid flow in a conduit using measurement circuits, the method comprising:

generating a first pair of ultrasonic frequency signals for simultaneous transmission through the conduit from a first pair of transducers, wherein the transducers in the first pair of transducers are positioned outside a circumference of the conduit to transmit the first pair of ultrasonic frequency signals to each other through the conduit;

receiving the first pair of ultrasonic frequency signals as a first pair of time-shifted ultrasonic frequency signals;

calculating a first transit time measurement based on the first pair of time-shifted ultrasonic frequency signals;

generating a second pair of ultrasonic frequency signals for simultaneous transmission through the conduit from a second pair of transducers, wherein the transducers of the second pair of transducers are positioned outside the circumference of the conduit to transmit the second pair of ultrasonic frequency signals to each other through the conduit;

receiving the second pair of ultrasonic frequency signals as a second pair of time-shifted ultrasonic frequency signals;

calculating a second transit time measurement based on the second pair of time-shifted ultrasonic frequency signals; and compensating the first and second transit time measurements by:

calculating a ratio based on the first and second transit time measurements;

determining error compensation factors using the ratio; and calculating flow velocity and volumetric fluid flow.

14. The method of claim 13, wherein compensating the first and the second time measurements comprises telemetering the first and second time measurements to a remote processor for error detection, flow velocity and volumetric fluid flow calculations.

15. The method of claim 14, wherein determining error compensation factors comprises retrieving angle error values from a look-up table.

16. The method of claim 14, wherein determining error compensation factors comprises calculating angle error values using mathematical functions.

17. The method of claim 14, wherein error detection includes calculating a ratio based on the first and second transit time measurements, using the ratio to retrieve error compensation factors and calculating flow velocity and volumetric fluid flow.

18. The method of claim 13, wherein determining error compensation factors comprises retrieving angle error values from a look-up table.

19. The method of claim 13, wherein determining error compensation factors comprises calculating angle error values using mathematical functions.

20. The method of claim 13, wherein using the ratio to retrieve error compensation factors comprises using the ratio to retrieve error angle estimates.

21. The method of claim 13, wherein generating a first pair of ultrasonic frequency signals and generating a second pair of ultrasonic frequency signals is performed simultaneously.

22. A method of estimating fluid flow in a conduit, the method comprising:

generating a first pair of ultrasonic frequency signals for transmission through the conduit from a first pair of transducers, wherein the transducers in the first pair of transducers are positioned outside a circumference of the conduit to transmit the first pair of ultrasonic frequency signals to each other through the conduit;

receiving the first pair of ultrasonic frequency signals as a first pair of time-shifted ultrasonic frequency signals;

calculating a first transit time measurement based on the first pair of time-shifted ultrasonic frequency signals;

generating a second pair of ultrasonic frequency signals for simultaneous transmission through the conduit from a second pair of transducers, wherein the transducers of the second pair of transducers are positioned outside the circumference of the conduit to transmit the second pair of ultrasonic frequency signals to each other through the conduit;

receiving the second pair of ultrasonic frequency signals as a second pair of time-shifted ultrasonic frequency signals;

calculating a second transit time measurement based on the second pair of time-shifted ultrasonic frequency signals; and compensating the first and second transit time measurements by:

calculating a ratio based on the first and second transit time measurements;

when the ratio is equal to one, calculating volumetric fluid flow; and when the ratio is less than or greater than one, performing error compensation calculations.

23. The method of claim 22, wherein generating a first pair of ultrasonic frequency signals and generating a second pair of ultrasonic frequency signals is performed simultaneously.

24. The method of claim 22, wherein compensating the first and second time measurements comprises transmitting the first and second transit time measurements to a processor for error compensation.

25. The method of claim 22, wherein performing error compensation calculations comprises using the error ratio to retrieve error correction factors and calculating corrected first and second time measurements based on the error correction factors.

26. The method of claim 22, wherein performing error compensation calculations comprises using the error ratio to calculate error correction factors and calculating corrected first and second time measurements based on the error correction factors.

27. The method of claim, 25, further comprises calculating flow velocity and estimating volumetric fluid flow using the corrected first and second time measurements.

28. The method of claim 26, further comprises calculating flow velocity and estimating volumetric fluid flow using the corrected first and second time measurements.

29. The method of claim 22, wherein compensating the first and second time measurements comprises transmitting the first and second transit time measurements to a remote signal processor for error compensation.

30. A method of estimating fluid flow in a conduit using a four crystal probe, the method comprising:

generating two transit time measurements;

compensating the transit time measurements using a predetermined compensation factor based on a ratio of the transit time measurements; and generating flow measurements and estimating volumetric fluid flow based on the flow measurement.

31. The method of claim 30, wherein compensating the transit time measurements comprises:

detecting an error in the transit time measurements;

calculating the compensation factor based on the transit time measurements;

using the compensation factor to calculate corrected transit time measurements.

32. A method of estimating fluid flow in a conduit, the method comprising:

generating a first pair of ultrasonic frequency signals for transmission, through the conduit, from the first pair of transducers, wherein the transducers of the first pair of transducers are positioned outside a circumference of the conduit to transmit the first pair of ultrasonic frequency signals to each other through the conduit;

receiving the first pair of ultrasonic frequency signals as a first pair of time-shifted ultrasonic frequency signals;

calculating a first transit time measurement based on the first pair of time-shifted ultrasonic frequency signals;

generating a second pair of ultrasonic frequency signals for transmission, through the conduit, from the second pair of transducers, wherein the transducers of the second pair of transducers are positioned outside the circumference of the conduit to transmit the second pair of ultrasonic frequency signals to each other through the conduit;

receiving the second pair of ultrasonic frequency signals as a second pair of time-shifted ultrasonic frequency signals;

calculating a second transit time measurement based on the second pair of time-shifted ultrasonic frequency signals; and compensating the first and second transit time measurements using a compensation factor selected based on a ratio of the first and second transit time measurements.

33. The method of claim 32, wherein generating a first pair of ultrasonic frequency signals and generating a second pair of ultrasonic frequency signals is performed simultaneously.

* * * * *